United States Patent [19]

Ringsdorf et al.

[11] 4,182,800

[45] Jan. 8, 1980

[54] METHOTREXATE-DIVINYL ETHER—MALEIC ANHYDRIDE COPOLYMER REACTION PRODUCT

[75] Inventors: Helmut Ringsdorf; Michael Przybylski, both of Mainz, Fed. Rep. of Germany

[73] Assignee: Hercules Incorporated, Wilmington, Del.

[21] Appl. No.: 920,312

[22] Filed: Jun. 28, 1978

[30] Foreign Application Priority Data

Jul. 16, 1977 [GB] United Kingdom ............... 29957/77
Apr. 1, 1978 [GB] United Kingdom ............... 12820/78

[51] Int. Cl.² .................................................. C08F 8/30
[52] U.S. Cl. ...................................... 525/375; 525/328

[58] Field of Search ................................... 526/50, 15

[56] References Cited

U.S. PATENT DOCUMENTS

| | | | |
|---|---|---|---|
| 3,224,943 | 12/1965 | Espy | 167/78 |
| 3,749,771 | 7/1973 | Regelson | 424/78 |
| 3,794,622 | 2/1974 | Breslow | 260/78.5 BB |
| 3,859,433 | 1/1975 | Regelson | 424/85 |

*Primary Examiner*—William F. Hamrock
*Attorney, Agent, or Firm*—Marion C. Staves

[57] ABSTRACT

Methotrexate can be reacted with cyclic copolymers of divinyl ether and maleic anhydride to prepare reaction products which are useful in retarding the growth of malignant tumors.

3 Claims, No Drawings

METHOTREXATE-DIVINYL ETHER—MALEIC ANHYDRIDE COPOLYMER REACTION PRODUCT

This invention relates to reaction products of methotrexate and cyclic copolymers of divinyl ether and maleic anhydride, their preparation and use in retarding the growth of malignant tumors.

Copolymers prepared from divinyl ether and maleic anhydride in mole ratios of 1:2 are known in the art and have been described as retarding the growth of tumors in U.S. Pat. No. 3,224,943, in preventing foot-and-mouth disease in U.S. Pat. No. 3,749,771, in preventing infection by Herpes virus in U.S. Pat. No. 3,859,433. A preferred type of narrow molecular weight copolymer is described in U.S. Pat. No. 3,794,622.

Previous pharmacological investigations with the copolymers established that toxicity, antitumor activity, and immune-potentiating effect are dependent on the molecular weight and the molecular weight distribution of the polymer. Moreover, divinyl ether—maleic anhydride copolymers showed activity against various transplantable tumors in experimental animals, e.g., Lewis Lung Carcinoma and Adenocarcinoma 755, which are partially resistant to methotrexate.

Methotrexate is a chemically useful chemotherapeutic agent against cancer. Its chemical formula is:

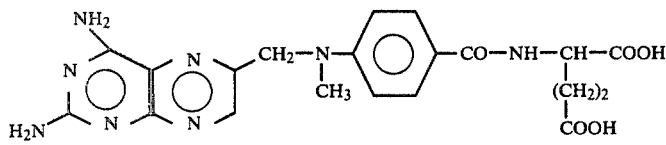

Methotrexate, i.e. N(p-[2,4-diamino-6-pteridinylmethyl]methylaminobenzoyl)glutamic acid, has been in clinical use for the treatment of various malignant as well as non-neoplastic diseases for many years. Considerable beneficial effects are achieved with methotrexate, either as a single agent or in combination with other drugs, e.g., in the treatment of choriocarcinoma, acute childhood leukemia, Burkitt's Lymphoma, and breast cancer. However, despite its wide range of clinical application, serious problems are associated with its use. Toxicity to normal tissues, particularly to bone marrow and small intestine, is often life-threatening. Development of resistance after initial use is frequently seen. Methotrexate shows unsatisfactory activity in animals against several solid tumors, such as Lewis Lung Carcinoma. It also exhibits severe immunosuppressive effects, which are typically observed within the class of antimetabolic cytotoxic agents. A large number of low molecular weight, structural analogs of methotrexate were synthesized and investigated in recent years, but for none of these derivatives was the therapeutic index (relative antitumor action to toxic action) superior to the parent drug.

It has now been found that methotrexate can be reacted chemically with divinyl ether—maleic anhydride copolymers, presumably by formation of an amide linkage between an amine group of the methotrexate and an acid group of the copolymer. The resulting product and its physiologically tolerated salts have lower toxicity than methotrexate itself and higher antitumor activity than a mixture of the two materials.

The reaction of methotrexate with a copolymer of divinyl ether and maleic anhydride will be conducted in an inert cosolvent, most preferably by slowly adding the methotrexate to an excess of the anhydride form of the copolymer. Typical inert cosolvents useful in the preparation of this invention are dimethyl sulfoxide, dimethylformamide, acetone, sulfolane, tetrahydrofuran, etc. As stated above, most preferably an excess of the copolymer, i.e. at least 1.2:1 anhydride groups to methotrexate, will be maintained. Time and temperature are not critical conditions to the reaction and will be obvious to those skilled in the art. In general the reaction will be conducted at a temperature above 0° C. and will require several hours to complete.

The ratio of methotrexate to copolymer in the reaction product will vary depending upon the anhydride content of the copolymer and reaction time. Relatively higher amounts of methotrexate can be bound to a copolymer when the copolymer used contains almost 100% anhydride. Purification of the reaction product of this invention can be carried out by usual procedures, such as solvent extraction and/or precipitation from solvents. It is believed the linkage of methotrexate to the copolymers can occur at either the 2- or 4-amino group of the pteridine ring since there is little if any difference in their chemical reactivity. It is also likely that methotrexate reacts randomly with the different types of anhydride groups present in the copolymers. However, no crosslinking due to reaction of both amino groups of methotrexate has been observed during the preparation of the reaction products of this invention.

The reaction products of methotrexate and copolymers of divinyl ether and maleic anhydride are useful in the treatment of all tumors which can be treated with methotrexate and the copolymers separately. In fact, studies of the anti-tumor activity of the reaction products of this invention indicate that their activity is greater than that of either methotrexate or the copolymers alone or mixtures of methotrexate and the copolymer.

Exemplary of the physiologically tolerated salts of the reaction products which are useful in this invention are the water-soluble salts of alkali metals, as for example, sodium, potassium, etc.; ammonium salts; salts of such amines as methylamine, dimethylamine, trimethylamine, ethylamine, diethylamine, tetraethylammonium, butylamine, methoxyamine, piperidine, morpholine, etc.; mixed salts containing ammonia and another amine.

While the reaction products exhibit effectiveness when administered either by the oral or parenteral route, treatment by the parenteral route will usually be preferred. The copolymers can be employed in aqueous solution or dissolved in physiological saline. In addition, various pharmaceutical preparations can be advantageously compounded which contain the active substance along with liquid or solid diluents. Solid preparations for extemporaneous dilution can be formulated employing various buffering agents as well as local anesthetics and other medicinal agents such as antibiotics, hypnotics, analgesics, etc., and inorganic salts to afford desirable pharmacological properties to the composition.

Dosages of the order of about 0.5 to 80 mg./kg. of the reaction product are desirable in inhibiting tumors in animals, and in human patients, depending on route of administration and duration of treatment. Since the reaction products are stable and widely compatible, they can be administered in solution or suspension in a variety of pharmacologically acceptable vehicles including water, propylene glycol, diethylcarbonate, glycerol, or oils such as peanut oil, sesame oil, olive oil, etc.

In addition to the conventional oral, intramuscular, subcutaneous, intravenous and intraperitoneal administration routes, these reaction products can also be employed in conjunction with profusion procedures wherein the tumor site is isolated from the main circulatory system for treatment.

In some cases it may be desirable to employ the reaction products in combination with one or more other carcinostatic agents. For this purpose, compositions containing from about 10 to 90% of the products are useful. Carcinostatic agents which can be employed in such combinations are well known in the art.

The following examples are presented to illustrate the invention. All parts and percentages are by weight unless otherwise indicated. Methotrexate used in the examples was obtained from the Drug Development Branch, National Cancer Institute, NIH, Bethesda, Maryland. The sample contained approximately 10% water, which was removed by extensive drying at 50° C. in vacuo over $P_2O_5$ in the dark. Unless otherwise indicated the divinyl ether—maleic anhydride copolymers used in the examples were prepared according to the procedures described in U.S. Pat. Nos. 3,224,943 and 3,794,622.

EXAMPLE 1

This example illustrates the preparation of a typical reaction product of methotrexate and divinyl ether—maleic anhydride copolymer.

Preparation of Copolymer

A polymerization vessel was charged with 10.3 parts of maleic anhydride, 200 parts of dry benzene and 7.45 parts of carbon tetrachloride. After dissolution of the maleic anhydride, the solution was sparged with nitrogen; 3.7 parts of freshly distilled divinyl ether in 60 parts of benzene was added. The reaction vessel was heated to 80° C. and a solution of 0.073 parts of benzoyl peroxide in 5.6 parts of benzene was added with agitation. The reaction was maintained at 80°–90° C. for four hours. The resulting slurry was cooled to 25°–30° C. and the swollen copolymer removed. The product was repeatedly extracted with a mixture of 7.5 parts benzene and 10 parts hexane, filtered, and vacuum-dried.

The resulting product was a 2:1 copolymer of maleic anhydride—divinyl ether, having an intrinsic viscosity of 1.65, a number average molecular weight of approximately 36,000 and an $\overline{M}_w/\overline{M}_n$ ratio of approximately 7.

Two parts of the copolymer prepared above were dissolved in 20 parts of freshly distilled dimethylformamide and one part of methotrexate disodium salt dissolved in 16 parts dimethylformamide was added to the solution at 20°. The reaction mixture was stirred at room temperature for 24 hours, then heated to 50° for three hours. The product was precipitated by adding the solution to 500 parts methylene dichloride, recovered by filtration and dried under vacuum for 20 hours. The product was purified by membrane dialysis of the hydrolyzed product. The product was dissolved in 400 parts of 0.05 N NaOH and dialyzed at 45 psi pressure against a membrane of about 1000 mol. wt. excluding size. This procedure was repeated four times after addition of 2 parts 0.05 N NaOH each time, after which only trace amounts of methotrexate were detected in the filtrate. The product was recovered from the caustic solution by adding it to an excess of acetone, the precipitate was filtered and dried under vacuum at 40°. There were 2.2 parts of the product obtained. It analyzed 11% methotrexate content by UV analysis.

EXAMPLE 2

This example illustrates another typical preparation of a reaction product of methotrexate and divinyl ether—maleic anhydride copolymer.

Preparation of Copolymer

A polymerization vessel was charged with 3.2 parts maleic anhydride and swept with nitrogen; 26.2 parts of dry acetone and 1.67 parts of freshly distilled, dry tetrahydrofuran were added, the solvents having been sparged with nitrogen and maintained under a nitrogen atmosphere. After dissolution of the maleic anhydride, 1.14 parts of divinyl ether in 1.58 parts of acetone was added. The reaction vessel was heated to 45° C. and a solution of 0.080 parts of azobis(isobutyronitrile) in 0.48 parts of acetone was added with agitation. The reaction was maintained at 45° C. for 8.75 hours. The resulting clear solution was filtered; the copolymer was precipitated by the addition of 27.0 parts of hexane, separated, repeatedly extracted with a mixture of 9.4 parts of benzene and 2.84 parts of hexane, filtered, and vacuum-dried.

The resulting product was a 2:1 copolymer of maleic anhydride—divinyl ether, having an intrinsic viscosity of 1.32 and a $\overline{M}_w/\overline{M}_n$ ratio of approximately 2.

Two parts of the copolymer prepared above were dissolved in 40 parts freshly distilled acetone. A solution of one part methotrexate dissolved in 30 parts dimethylsulfoxide was added slowly to this solution at 20°. The clear red reaction mixture was heated to 45° for four hours, then stirred for 72 hours after being allowed to cool to 20°. The product was precipitated by adding the solution to 600 parts methylene chloride, then redissolved in acetone and precipitated again from methylene chloride. The product was then purified further in a Soxhlet extractor with two 800 part changes of methylene chloride. It was then reprecipitated three times by dissolving in acetone and adding to methylene chloride, after which time no free methotrexate was detected in the precipitating solvent. Elemental analysis showed 44.36% carbon, 4.78% hydrogen, and 5.01% nitrogen. The methotrexate content as indicated by UV analysis was 25.2%. The product was soluble in water, acetone, methanol, dimethylformamide, and dimethylsulfoxide. It was insoluble in methylene chloride and diethyl ether.

EXAMPLES 3–5

These examples illustrate typical preparations of reaction products of methotrexate and divinyl ether—maleic anhydride copolymer.

In a typical run 1 part of divinyl ether—maleic anhydride copolymer is dissolved in 10 parts of freshly distilled dimethylformamide and about 0.5 part of methotrexate dissolved in 8 parts of dimethylformamide is added dropwise while stirring at room temperature. The reaction mixture is stirred for 24 to 48 hours at room temperature and finally heated for 3 hours at 50° C. In each case the product was precipitated in 250 parts of $CH_2Cl_2$, filtered, washed with methanol and dried overnight in vacuo. The crude reaction product is hydrolyzed to the polycarboxylate and dialyzed in 200 ml, and subsequently 4×100 ml, of 0.05 M NaOH (BM 10 membrane, Berghof, Tubingen, West Germany, exclusion size 1000). Only trace amounts of free methotrexate are then detectable in the filtrate. The reaction product is precipitated in 150 ml of acetone, washed with acetone and dried in vacuo over $P_2O_5$. The infrared spectrum of the reaction products exhibit amide and anhydride vibrations at 1640 and 1775 cm$^{-1}$. The ultraviolet spectrum maximum at 303 nm is used for the spectroscopic determination of methotrexate content in the reaction products. The molecular weight and anhydride content of the copolymers used in the reaction, the mole ratio of copolymers to methotrexate used in the reaction, reaction time, and methotrexate content of the reaction products are set forth in Table I.

hours the clear, orange-red reaction mixture is stirred for 24 to 96 hours at room temperature. The reaction product is precipitated in 300 parts of $CH_2Cl_2$, filtered and reprecipitated with acetone-dimethyl formamide/$CH_2Cl_2$. It is then extracted for 48 hours with 2×400 parts of $CH_2Cl_2$ in a Soxhlet extractor. Final purification is obtained by three-fold dissolution in acetone (70 parts), removal of acetone-insoluble material, and reprecipitation in $CH_2Cl_2$. The final product does not show free methotrexate on thin-layer chromatography, with ninhydrine-reactive material. It is soluble in $H_2O$ (after hydrolysis to the polycarboxylate), acetone, dimethylformamide and dimethylsulfoxide, and insoluble in $CH_2Cl_2$ and ether. The ultraviolet spectrum maximum at 303 nm is used for the spectroscopic determination of methotrexate content in the reaction products. The molecular weight and anhydride content of the copolymers used in the reaction, the mole ratio of copolymer to methotrexate used in the reaction, reaction time, and methotrexate content of the reaction products are set forth in Table II.

TABLE II

| | Copolymer | | Mole Ratio | Reaction | Methotrexate | Elemental Analysis of Product | | |
|---|---|---|---|---|---|---|---|---|
| Example | Molecular Weight | Anhydride % of Theory | Copolymer/ Methotrexate | Time, Hours | Content of Product[a] | C | H | N |
| 7 | Mn 9,600 Mw 18,100 | 63 | 3.55:1 | 24 | 3.5 | 34.9 | 3.7 | 0.3 |
| 8 | Mn 4,400 Mw 9,300 | 63 | 3.5:1 | 24 | 4 | 33.7 | 3.8 | 0.3 |
| 9 | Mn 24,000 Mw 53,000 | 99 | 3.1:1 | 72 | 25.2 | 44.4 | 4.8 | 5.0 |
| 10 | Mn 24,000 Mw 53,000 | 99 | 3.1:1 | 72 | 20 | 45.8 | 5.1 | 5.1 |
| 11 | Mn 24,000 Mw 53,000 | 99 | 1.9:1 | 96 | 42.6 | 46.1 | 5.2 | 8.4 |
| 12 | Mn 15,500 Mw 30,000 | 82 | 3.5:1 | 72 | 16.6 | 47.4 | 5.2 | 9.5 |

[a] % base-mol methotrexate/copolymer + methotrexate

TABLE I

| | Copolymer | | Mole Ratio | Reaction | Methotrexate | Elemental Analysis of Product | | |
|---|---|---|---|---|---|---|---|---|
| Example | Molecular Weight | Anhydride % of Theory | Copolymer/ Methotrexate | Time, Hours | Content of Product[a] | C | H | N |
| 3 | Mn 20,000 Mw 83,500 | 15 | 3.1:1 | 27 | 11 | 46.5 | 5.2 | 4.4 |
| 4 | Mn 9,100 Mw 34,300 | 33 | 3.46:1 | 24 | 3 | 29.0 | 3.0 | 0.3 |
| 5 | Mn 20,000 Mw 83,500 | 15 | 3.37:1 | 48 | 3.5 | 29.7 | 4.3 | 0.3 |

[a] % base-mol methotrexate/copolymer + methotrexate

EXAMPLE 6

This example is the same as Examples 3-5 except dimethylsulfoxide was used in place of dimethylformamide as the solvent in the reaction. The copolymer used in the reaction had an Mn 15,500, Mw 30,000 and contained 82% anhydride of theory. The copolymer is reacted with the methotrexate in a mole ratio of 3.5:1 for 24 hours. The reaction product contains 6.1% methotrexate and an elemental analysis of C 37.1, H 4.0, N 1.7.

EXAMPLES 7-12

These examples illustrate typical preparations of reaction products of methotrexate and divinyl ether—maleic anhydride copolymer.

In a typical run 1 part of divinyl ether—maleic anhydride copolymer is dissolved in 20 parts of acetone and about 0.55 part of methotrexate dissolved in 15 parts of dimethylsulfoxide is added dropwise while stirring at room temperature. After initial heating at 45° C. for 4

TUMOR TRANSPLANTATION AND CHEMOTHERAPY EXAMPLES

The reaction product and the divinyl ether—maleic anhydride copolymer described in Example 9 were used in all the following examples.

Six to eight weeks old male $CD2F_1$ mice (BALB/C female X DBA/2 male), weighing 20–25 g, were used in studies against leukemia L1210, and in other in vivo experiments. Male $B6D2F_1$ (C56BL/6×DBA/2) mice of 20–25 g weight were used in chemotherapy experiments against Lewis lung carcinoma. L1210 leukemia was maintained by continuous intraperitoneal passage, and was inoculated by intraperitoneal injection of 0.1 ml of ascites fluid containing $10^6$ viable cells/ml. Treatment of 10 mice per group was initiated 24 hours after tumor inoculation. Drugs were administered intraperitoneally at 0.01 mg/g body weight in 2% $NaHCO_3$. Antitumor activity was determined by comparing the median survival time of the treated group (T) with that of the control group (C), and expressed as percentage of increase in median life span (ILS), $$100\left(\frac{T}{C} - 1\right).$$

Lewis lung carcinoma was passaged subcutaneously in syngeneic C57BL/6 male mice, according to standard protocols of the Drug Research and Development Program, National Cancer Institute, and implanted subcutaneously at $10^6$ viable cells in the right thigh of B6D2F$_1$ mice. Drug treatment began 24 hours later, at 0.01 mg/g body weight administered intraperitoneally. Eight mice per treated group, and at least 16 mice per control group, were used in each experiment. The tumor growth was determined by measurement of perpendicular tumor diameters with a vernier caliper. Tumor measurements were made every second day after development of palpable tumors of approximately 50 mg. Tumor weight in mg was estimated using the formula for the volume of a prolate ellipsoid, under the assumption of unit density; mm major diameter × (mm minor diameter)$^2 \times \frac{1}{2}$.

Cultures of L1210 leukemia cells were initiated from tumors in CD2F$_1$ mice maintained as described above. L1210 cells were grown and assayed in Falcon culture flasks (Falcon Plastics Ltd., Oxnard, Ca.) in RMPI 1630 medium supplemented with 10% fetal calf serum (Grand Island Biological Co., Grand Island, N.Y.). Cell numbers in culture were determined with a Coulter counter (Coulter Electronics Inc. Fl.) by removing 0.5 ml aliquots from the culture flasks. Stock cultures were counted and diluted to a concentration of $10^5$ viable (trypan blue) cells/ml with a total of 10 ml in each flask. Drugs were dissolved immediately before each experiment in sterile 2% by weight NaHCO$_3$ to obtain stock solutions. Appropriate dilutions were made with culture medium so that the final concentration of NaHCO$_3$ in the cell culture was not greater than 1%. Cells were exposed to drugs at various concentrations and counted after 48 hours. Growth inhibitory effects of each drug were evaluated at least twice, with triplication at each concentration, and the results expressed as mean ±S.E. of the percent inhibition compared to nontreated controls.

The results of the studies against leukemia L1210 in vivo are set forth in Table III. The results of the studies against leukemia L1210 in vitro are set forth in Table IV. The results of the studies against Lewis lung carcinoma in vivo are set forth in Table V.

TABLE III

Antitumor Activity of MTX*, DIVEMA** + MTX, and DIVEMA-MTX Against Mulrine L1210 Leukemia

| Drug | Dose (mg/kg)$^a$ day MTX | DIVEMA | Schedule (days) | Max. Wt. Loss (%) | Survival time (days) Median | Range | % ILS | Long-term Survival$^b$ |
|---|---|---|---|---|---|---|---|---|
| Untreated control | | | | — | 8.5 ± 0.3$^c$ | 8–10 | — | — |
| MTX | 5 | | 1,5,9,13 | 1.0 | 12.4$^d$ | 11–17 | 46 | 0/20 |
| | 8 | | 1,5,9,13 | 1.5 | 16.8$^d$ | 16–22 | 98 | 0/20 |
| | 10 | | 1,5,9,13,17 | 2.8 | 17.5$^d$ | 16–23 | 106 | 0/20 |
| | 15 | | | 12.3 | 19.8$^d$ | 18–26 | 133 | 0/20 |
| | 20 | | | 16.0 | 22.5$^d$ | 15–28 | 165 | 0/20 |
| | 30 | | 1,5,9,13 | 27.0 | 13.5 | 9–24 | toxic | 0/20 |
| DIVEMA | | 19.6 | 1,5,9 | 4.2 | 9.5 | 9–11 | 12 | 0/10 |
| | | 39.2 | | 7.0 | 9.8 | 9–12 | 15 | 0/10 |
| | | 78.4 | | 11.0 | 10.5 | 2–12 | 24 | 0/10 |
| MTX + DIVEMA | 5 | 14.5 | 1,5,9,13 | 3.4 | 16.5$^d$ | 12–20 | 94 | 0/20 |
| | 8 | 23.4 | 1,5,9,13,17 | 4.8 | 19.0$^d$ | 12–26 | 124 | 0/20 |
| | 10 | 29.2 | | 4.6 | 20.0$^d$ | 17–25 | 135 | 0/20 |
| | 15 | 43.8 | | 15.1 | 20.6$^d$ | 17–27 | 142 | 0/20 |
| | 20 | 58.4 | 1,5,9,13,17 | 16.6 | 20.0$^d$ | 17–25 | 135 | 0/20 |
| | 10 | 14.6 | | | 20.5 | 17–30 | 141 | 0/10 |
| | 20 | 14.6 | | | 20.0 | 13–29 | 135 | 0/10 |
| | 30 | 14.6 | 1,5,9 | | 11.5 | 9–27 | toxic | 0/10 |
| DIVEMA - MTX | 5 | 14.6 | 1,5,9,13,17 | 4.2 | 20.5$^d$ | 17–>30 | 141 | 2/20 |
| | 8 | 23.4 | | 10.0 | 26.0$^d$ | 18–>30 | 206 | 5/20 |
| | 10 | 29.2 | | 13.0 | 18.0$^d$ | 12∞>30 | 112 | 3/20 |
| | 20 | 58.4 | 1,5,9 | 27.4 | 13.5 | 9–17 | toxic | 0/10 |

*Methotrexate
**Divinyl ether–maleic anhydride copolymer
$^a$doses of DIVEMA-MTX are expressed as MTX and DIVEMA equivalents. The sum of these figures represents the total does of DIVEMA-MTX.
$^b$>30 days; $^c$mean ± S.D. from six individual control groups; $^d$mean from two individual treatment groups; coefficient of variation was never greater than 6%.

TABLE IV

Growth Inhibition of L1210 Cells in Culture After Exposure to MTX*, DIVEMA**-MTX and DIVEMA + MTX

| Drug Concentration (μg/ml)$^a$ | | Concentration DIVEMA-MTX | Percent of Control Growth + S.E. | | |
|---|---|---|---|---|---|
| MTX | DIVEMA | MTX Alone | DIVEMA + MTX Reaction Product | DIVEMA Combination | Alone |
| 0.00454 | 0.01326 | 118.6 ± 11.6 | 147.3 ± 6.3 | 107.6 ± 3.7 | |
| 0.0454 | 0.1326 | 37.2 ± 4.5 | 45.0 ± 2.0 | 41.1 ± 3.2 | |
| 0.454 | 1.326 | 28.2 ± 4.3 | 37.0 ± 2.4 | 24.4 ± 1.1 | |
| 4.54 | 25.3 ± 3.7 | 30.0 ± 3.1 | 21.3 ± 0.8 | | |

TABLE IV-continued

Growth Inhibition of L1210 Cells in Culture After Exposure to MTX*, DIVEMA**-MTX and DIVEMA + MTX

| Drug Concentration | | | Percent of Control Growth ± S.E. | | |
|---|---|---|---|---|---|
| ($\mu$g/ml)$^a$ | | Concentration DIVEMA-MTX | DIVEMA + MTX | DIVEMA | |
| MTX | DIVEMA | MTX Alone | Reaction Product | Combination | Alone |
| | 132.6 | | | | 101.2 ± 9.7 |

*Methotrexate
**Divinyl ether–maleic anhydride copolymer
$^a$Concentrations for DIVEMZ-MTX are expressed as MTX and DIVEMA equivalents.

TABLE V

Effect of DIVEMA*, DIVEMA-MTX** and DIVEMA + MTX Against Subcutaneous Lewis Lung Carcinoma

| Drug | Dose (mg/kg/day) | | Schedule (Days) | Tumor growth delay (days)$^b$ | Tumor Wt. Inhibition$^c$ (%) | Survival Time (days) | |
|---|---|---|---|---|---|---|---|
| | MTX$_a$ | DIVEMA | | | | Median | Range |
| Untreated control | — | — | | | | 26.0 | 22–36 |
| MTX | 2 | | 1–8 | — | — | 28.0 | 20–36 |
| DIVEMA | | 5.84 | | — | — | 27.0 | 21–46 |
| MTX + DIVEMA | 2 | + 5.84 | | 1.0 | 16 | 26.5 | 18–45 |
| DIVEMA-MTX | 2 | 5.84 | | 2.5 | 33 | 36.5 | 30–43 |

*Divinyl ether - maleic anhydride copolymer
**Methotrexate
$^a$Dosages of DIVEMA-MTX are given in MTX and DIVEMA equivalents.
$^b$Difference in treated group compared to untreated control group to reach a mean tumor weight of 3 g.
$^c$100 × (1-mean tumor weight of treated group on day 19/mean tumor weight of controls on day 19).

What we claim and desire to protect by Letters Patent is:

1. The reaction product of methotrexate and divinyl ether—maleic anhydride copolymer produced by reacting methotrexate with an excess of the anhydride form of divinyl ether—maleic anhydride copolymer in an inert cosolvent at a temperature above 0° C., said copolymer containing divinyl ether to maleic anhydride in a mole ratio of 1:2.

2. The physiologically tolerated salts of the reaction product of claim 1.

3. The process of preparing the reaction product of methotrexate and divinyl ether—maleic anhydride copolymer which comprises reacting methotrexate with an excess of at least 1.2:1 of anhydride groups in the copolymer to methotrexate in an inert cosolvent at a temperature above 0° C., said copolymer containing divinyl ether to maleic anhydride in a mole ratio of 1:2.

* * * * *

UNITED STATES PATENT AND TRADEMARK OFFICE
CERTIFICATE OF CORRECTION

PATENT NO. : 4,182,800
DATED : January 8, 1980
INVENTOR(S) : Helmut Ringsdorf & Michael Przybylski It is certified that error appears in the above-identified patent and that said Letters Patent are hereby corrected as shown below:

Column 8, last line in Table $\overline{IV}$ under DIVEMA "25.3 $\pm$ 3.7" should read --13.26--.

Column 8, last line in Table $\overline{IV}$ under MTX ALONE "30.0 $\pm$ 3.1" should read --25.3 $\pm$ 3.7--.

Column 8, last line in Table $\overline{IV}$ under REACTION PRODUCT "21.3 $\pm$ 0.8" should read --30.0 $\pm$ 3.1--.

Column 8, last line in Table $\overline{IV}$ under COMBINATION "is blank" should read --21.3 $\pm$ 0.8--.

Signed and Sealed this

*Fifteenth* Day of *April 1980*

[SEAL]

*Attest:*

*Attesting Officer*

SIDNEY A. DIAMOND

*Commissioner of Patents and Trademarks*